United States Patent
Aguilar Flores et al.

(10) Patent No.: US 11,850,342 B2
(45) Date of Patent: Dec. 26, 2023

(54) SECURING CONNECTIONS TO DIALYZERS

(71) Applicant: Fresenius Medical Care Holdings, Inc., Waltham, MA (US)

(72) Inventors: Jose Omar Aguilar Flores, Pharr, TX (US); Diego Suarez del Real Pena, Mission, TX (US); Irving Uziel Hernandez Gomez, Hidalgo, TX (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 121 days.

(21) Appl. No.: 17/699,627

(22) Filed: Mar. 21, 2022

(65) Prior Publication Data

US 2023/0293791 A1    Sep. 21, 2023

(51) Int. Cl.
  *A61M 1/16* (2006.01)
  *F16L 33/10* (2006.01)

(52) U.S. Cl.
  CPC .......... *A61M 1/1652* (2014.02); *F16L 33/10* (2013.01)

(58) Field of Classification Search
  CPC ........ A61M 1/1652; F16L 33/10; F16L 33/02
  USPC ........................................ 285/403, 325, 305
  See application file for complete search history.

(56) References Cited

U.S. PATENT DOCUMENTS

| | | | |
|---|---|---|---|
| 1,989,823 A | 2/1935 | Raabe | |
| 2,036,087 A | 3/1936 | Chapman | |
| 4,230,109 A | 10/1980 | Geiss | |
| 4,340,052 A | 7/1982 | Dennehey et al. | |
| 4,826,486 A | 5/1989 | Palsrok et al. | |
| 4,997,421 A * | 3/1991 | Palsrok | A61M 39/1011 604/174 |
| 5,037,405 A | 8/1991 | Crosby | |
| 5,040,831 A | 8/1991 | Lewis | |
| 5,192,273 A | 3/1993 | Bierman | |
| 5,248,306 A | 9/1993 | Clark et al. | |
| 5,290,248 A | 3/1994 | Bierman et al. | |

(Continued)

FOREIGN PATENT DOCUMENTS

| | | |
|---|---|---|
| CH | 716220 A2 | 11/2020 |
| CN | 109806455 A | 5/2019 |

(Continued)

OTHER PUBLICATIONS

EPO/ISA, "PCT Application No. PCT/US23/64346, International Search Report and Written Opinion," 9 pages.

*Primary Examiner* — David Bochna
(74) *Attorney, Agent, or Firm* — Bass Patent Law, LLC

(57) ABSTRACT

The present teachings include techniques for securing a connection to a dialyzer or the like—e.g., securing the junction between a dialyzer port and a connector (e.g., a DIN connector) that couples the port to tubing of an extracorporeal circuit of a hemodialysis system. To this end, a locking device may engage both a DIN connector and a portion of the dialyzer, such as the cap or an adapter engaged therewith. The locking device may include an interior void sized and shaped to accommodate winged portions (or other portions) of the DIN connector to mitigate rotation thereof relative to the port to which it is engaged. Further, the locking device may be used to ensure that coupling between the DIN connector and the port is proper and secure. In this manner, a locking device can mitigate leaks, which can be catastrophic during a hemodialysis treatment or the like.

20 Claims, 10 Drawing Sheets

(56) References Cited

U.S. PATENT DOCUMENTS

| | | | |
|---|---|---|---|
| 5,314,411 A | 5/1994 | Bierman et al. | |
| 5,350,201 A | 9/1994 | Bynum | |
| 5,354,282 A | 10/1994 | Bierman | |
| 5,456,671 A | 10/1995 | Bierman | |
| 5,578,013 A | 11/1996 | Bierman | |
| 5,702,371 A | 12/1997 | Bierman | |
| 5,765,877 A | 6/1998 | Sakane et al. | |
| 5,800,402 A * | 9/1998 | Bierman | A61M 25/02 604/174 |
| 5,827,230 A | 10/1998 | Bierman | |
| 5,833,667 A | 11/1998 | Bierman | |
| 5,947,931 A | 9/1999 | Bierman | |
| 5,957,894 A | 9/1999 | Kerwin et al. | |
| 6,267,754 B1 | 7/2001 | Peters | |
| 6,290,676 B1 | 9/2001 | Bierman | |
| 6,309,543 B1 | 10/2001 | Fenton et al. | |
| 6,375,231 B1 | 4/2002 | Picha et al. | |
| 6,508,807 B1 | 1/2003 | Peters | |
| 6,786,892 B2 | 9/2004 | Bierman | |
| 6,827,705 B2 | 12/2004 | Bierman | |
| 6,837,875 B1 | 1/2005 | Bierman | |
| 7,481,463 B2 * | 1/2009 | Ishida | F16L 41/08 285/403 |
| 7,614,123 B2 | 11/2009 | Schweikert | |
| D618,792 S | 6/2010 | Bierman | |
| 7,744,572 B2 | 6/2010 | Bierman | |
| 7,758,082 B2 | 7/2010 | Weigel et al. | |
| D622,841 S | 8/2010 | Bierman | |
| 7,799,015 B2 | 9/2010 | Schweikert | |
| 7,827,656 B2 | 11/2010 | Schweikert | |
| 7,874,595 B2 * | 1/2011 | Lechner | F16L 37/133 285/305 |
| 7,887,515 B2 | 2/2011 | Bierman | |
| 7,967,792 B2 | 6/2011 | Bierman | |
| 8,042,838 B2 | 10/2011 | Buckler et al. | |
| 8,087,702 B2 | 1/2012 | Schmidt | |
| 8,141,914 B2 * | 3/2012 | Haltmayer | F16L 37/144 285/403 |
| 8,585,096 B2 | 11/2013 | Schnell et al. | |
| D710,996 S | 8/2014 | Bayly | |
| 9,097,370 B2 | 8/2015 | Schnell et al. | |
| 10,213,590 B2 | 2/2019 | Herrig | |
| 10,632,296 B2 | 4/2020 | Herrig | |
| 11,179,556 B2 | 11/2021 | Fantuzzi et al. | |
| 2001/0011164 A1 | 8/2001 | Bierman | |
| 2002/0133121 A1 | 9/2002 | Bierman | |
| 2002/0149200 A1 | 10/2002 | Fumioka | |
| 2005/0006297 A1 | 1/2005 | Moriwaki et al. | |
| 2005/0034729 A1 | 2/2005 | Dombrowski | |
| 2005/0075610 A1 | 4/2005 | Bierman | |
| 2005/0120523 A1 | 6/2005 | Schweikert | |
| 2005/0253390 A1 | 11/2005 | Blazek | |
| 2007/0075003 A1 | 4/2007 | Schmidt | |
| 2007/0149930 A1 | 6/2007 | Bierman | |
| 2007/0173768 A2 | 7/2007 | Bierman | |
| 2007/0276333 A1 | 11/2007 | Bierman | |
| 2008/0129042 A1 | 6/2008 | Weigel et al. | |
| 2009/0261581 A1 | 10/2009 | Schmidt | |
| 2009/0264867 A1 | 10/2009 | Schweikert | |
| 2009/0264868 A1 | 10/2009 | Schweikert | |
| 2010/0051529 A1 | 3/2010 | Grant et al. | |
| 2010/0228231 A1 | 9/2010 | Weigel et al. | |
| 2011/0084479 A1 | 4/2011 | Schmidt | |
| 2012/0041378 A1 | 2/2012 | Bierman | |
| 2012/0214337 A1 | 8/2012 | Schnell et al. | |
| 2013/0060268 A1 | 3/2013 | Herrig | |
| 2014/0035273 A1 | 2/2014 | Schnell et al. | |
| 2014/0263018 A1 | 9/2014 | Fuhriman | |
| 2015/0157845 A1 | 6/2015 | Bayly | |
| 2016/0069495 A1 | 3/2016 | Statler, III et al. | |
| 2017/0312492 A1 | 11/2017 | Fantuzzi et al. | |
| 2019/0184151 A1 | 6/2019 | Herrig | |
| 2019/0217076 A1 | 7/2019 | O'Neil | |
| 2019/0247559 A1 | 8/2019 | Mochizuki | |
| 2021/0131596 A1 | 5/2021 | Mitrovic et al. | |
| 2021/0268255 A1 | 9/2021 | O'Neil | |

FOREIGN PATENT DOCUMENTS

| | | |
|---|---|---|
| CN | 211068331 U | 7/2020 |
| EP | 2269563 B1 | 4/2016 |
| JP | 2004041612 A | 2/2004 |
| WO | 2019002066 A3 | 3/2019 |
| WO | 2020240150 A1 | 12/2020 |
| WO | 2021214125 A1 | 10/2021 |
| WO | 2023183736 A1 | 9/2023 |

* cited by examiner

SECURING CONNECTIONS TO DIALYZERS

FIELD

The present disclosure generally relates to securing connections to dialyzers and the like, e.g., using a lock adapter structurally configured to secure the engagement between a dialyzer and a connector complying with standards set by the German Institute for Standardisation (DIN) for extracorporeal circuits of dialysis systems.

BACKGROUND

During a hemodialysis treatment, and/or other treatments using extracorporeal circuits and the like, a coupling between the dialyzer and the connector from a tubing set is typically one of the most critical joints in the system. This specific junction may be critical because it can be associated with a relatively high-rate of uncoupling and/or leaking in a hemodialysis treatment, which can lead to disastrous outcomes. By way of example, leaks or otherwise uncoupling of this dialyzer/tubing connector can not only lead to a failure in a treatment, but air infiltrating an extracorporeal circuit can lead to an embolism or worse. There remains a need for improved techniques to secure connections to dialyzers and the like.

SUMMARY

The present teachings include techniques for securing a connection to a dialyzer or the like—e.g., securing the junction between a dialyzer port and a connector (e.g., a DIN connector) that couples the port to tubing of an extracorporeal circuit of a hemodialysis system. To this end, a locking device may engage both a DIN connector and a portion of the dialyzer, such as the cap or an adapter engaged therewith. The locking device may include an interior void sized and shaped to accommodate winged portions (or other portions) of the DIN connector to mitigate rotation thereof relative to the port to which it is engaged. Further, the locking device may be used to ensure that coupling between the DIN connector and the port is proper and secure. In this manner, a locking device can mitigate leaks, which can be catastrophic during a hemodialysis treatment or the like.

In an aspect, a system disclosed herein may include a locking device featuring: a housing including a top surface, a bottom surface, and a side portion disposed between the top surface and the bottom surface; a cutout disposed through the housing from the top surface to the bottom surface, the cutout at the bottom surface sized and shaped to accommodate a port of a dialyzer, and the cutout at the top surface sized and shaped to accommodate one or more of (i) an outer diameter of tubing of an extracorporeal circuit of a dialysis system, and (ii) an outer diameter of a first end of a connector configured to couple the tubing to the port of the dialyzer, where a second end of the connector is configured to releasably secure the connector to the port of the dialyzer; an interior void within the side portion between the top surface and the bottom surface of the housing, the interior void having a maximum diameter larger than a maximum width of the cutout, the interior void sized and shaped to accommodate winged portions disposed between the first and second ends of the connector; and a first engagement portion disposed on the bottom surface of the housing. The system may also include a second engagement portion on an end of the dialyzer that includes the port, where the first engagement portion and the second engagement portion are couplable such that the winged portions of the connector are mitigated from rotating relative to the end of the dialyzer thereby securing the connector in a substantially fixed rotational position.

Implementations may include one or more of the following features. The second engagement portion may be integral with a housing of the dialyzer. The second engagement portion may be disposed on an adapter couplable to the dialyzer.

In an aspect, a device disclosed herein for securing a connection to a dialyzer may include: a housing including a top surface, a bottom surface, and a side portion disposed between the top surface and the bottom surface; a cutout disposed through the housing from the top surface to the bottom surface, the cutout at the bottom surface sized and shaped to accommodate a port of a dialyzer, and the cutout at the top surface sized and shaped to accommodate one or more of (i) an outer diameter of tubing of an extracorporeal circuit of a dialysis system, and (ii) an outer diameter of a first end of a connector configured to couple the tubing to the port of the dialyzer, where a second end of the connector is configured to releasably secure the connector to the port of the dialyzer; an interior void within the side portion between the top surface and the bottom surface of the housing, the interior void having a maximum diameter larger than a maximum width of the cutout, the interior void sized and shaped to accommodate winged portions disposed between the first and second ends of the connector; and a first engagement portion disposed on the bottom surface of the housing, the first engagement portion structurally configured to couple to a second engagement portion disposed on an end of the dialyzer that includes the port such that, when coupled, the connector is at least partially disposed within the interior void and the winged portions of the connector are mitigated from rotating relative to the end of the dialyzer thereby securing the connector in a substantially fixed rotational position.

Implementations may include one or more of the following features. The device may further include an adapter structurally configured to secure to the end of the dialyzer that includes the port, the adapter including the second engagement portion thereon. The device may further include an extension engaged with the adapter, the extension including a mating feature structurally configured to couple with a portion of a dialysis system. The mating feature may be adjustable along the extension, and the mating feature may include one or more of a clamp and a clip structurally configured to couple with at least one of a dialysate port and dialysate tubing of the dialysis system. The adapter may have an annular shape structurally configured to be disposed about the port of the dialyzer. The second engagement portion may be disposed at least partially around the annular shape of the adapter. The first engagement portion may include at least one of: a void structurally configured to receive a projection of the second engagement portion, and a projection structurally configured to be received within a void of the second engagement portion. The first engagement portion may include at least one of: a slot structurally configured to slidably receive a rail of the second engagement portion, and a rail structurally configured to be slidably received by a slot of the second engagement portion. One or more of the cutout, the interior void, and the first engagement portion may be structurally configured to prevent at least one of coupling with the second engagement portion and receiving the winged portions of the connector within the interior void unless the connector is in a predetermined position relative to the port of the dialyzer. The predetermined position may be a fully seated position of the connector within the port of the dialyzer. The connector may comply with standards set by the German Institute for Standardisation (DIN) for extracorporeal circuits of dialysis systems. The port of the dialyzer may be an inlet port or an outlet port. A cross-section of at least a portion of the interior void may have substantially the same shape as a cross-section of the connector disposed through the winged portions thereof. The first engagement portion may wholly form the bottom surface of the housing.

In an aspect, a method disclosed herein may include: releasably securing a connector to a port of a dialyzer such that the connector is in a predetermined position relative to the port, the connector having one or more winged portions disposed between first and second ends thereof; and engaging a locking device with at least one of the port and the connector. Engaging the locking device may include coupling a first engagement portion disposed on the locking device to a second engagement portion disposed on an end of the dialyzer that includes the port, and receiving at least a portion of the one or more winged portions of the connector within an interior void of a housing of the locking device.

Implementations may include one or more of the following features. The method may further include securing an adapter to the end of the dialyzer that includes the port, the adapter including the second engagement portion. Securing the adapter may include coupling a mating feature thereof with a portion of a dialysis system.

These and other features, aspects, and advantages of the present teachings will become better understood with reference to the following description, examples, and appended claims.

BRIEF DESCRIPTION OF THE DRAWINGS

The foregoing and other objects, features, and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein. In the drawings, like reference numerals generally identify corresponding elements.

DETAILED DESCRIPTION

Figure 2:
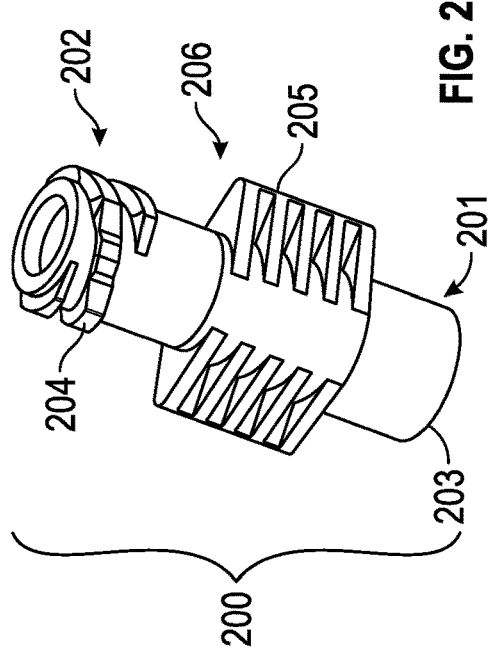
FIG. 2 illustrates a connector.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "about," "approximately," or "substantially" when used in reference to physical characteristics, should be understood to contemplate a range of deviations that would be appreciated by one of ordinary skill in the art to operate satisfactorily for a corresponding use, function, purpose, or the like. Ranges of values and/or numeric values are provided herein as examples only, and do not constitute a limitation on the scope of the described embodiments. Where ranges of values are provided, they are also intended to include each value within the range as if set forth individually, unless expressly stated to the contrary. The use of any and all examples, or exemplary language ("e.g.,"

"such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "front," "rear," "top," "bottom," "up," "down," and the like, are words of convenience and are not to be construed as limiting terms unless specifically stated to the contrary.

In general, the devices, systems, kits, and methods disclosed herein may generally relate to securing a connection to a dialyzer and the like. That is, the present disclosure generally relates to securing connections to dialyzers, which may include the use of a lock adapter structurally configured to secure the engagement between a dialyzer and a connector complying with standards set by the German Institute for Standardisation (DIN) for extracorporeal circuits of dialysis systems. Thus, an aspect of the present teachings includes a lock adapter structurally configured to secure and/or maintain a relative position (and thus a connection) of a DIN connector and a dialyzer. However, it will be understood that, while the present disclosure may emphasize securing a connection to a dialyzer, and more particularly the present disclosure may emphasize securing the junction between a DIN connector and a port of a dialyzer, the present teachings may also or instead be adapted for use in securing other connections, junctions, ports, and the like of a dialyzer and/or other similar devices, machines, and systems.

Figure 1:
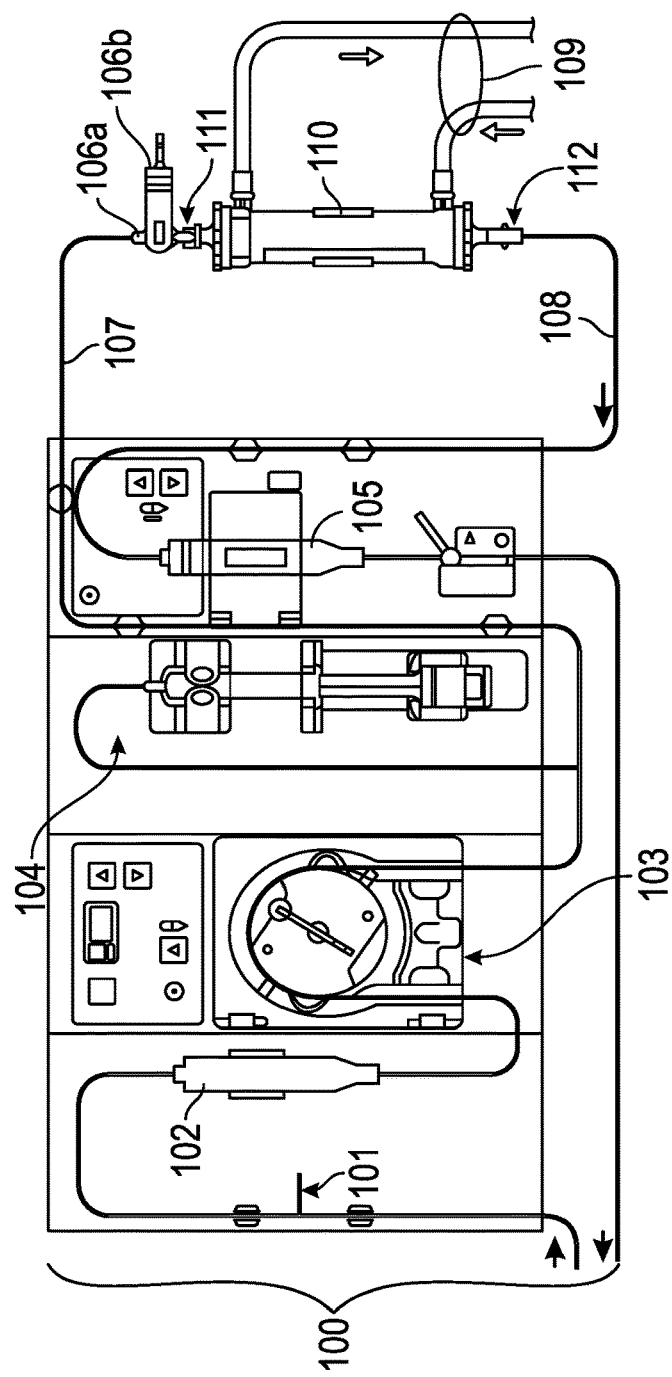
FIG. 1 illustrates a dialysis treatment system.

Before describing specific embodiments of the present teachings, it may be useful to provide context for certain use-cases of the present teachings. To that end, FIG. 1 illustrates a dialysis treatment system. The system 100 of FIG. 1 is a useful example schematic of a setup for dialysis treatment, and includes some common components of such a setup including, for example, a priming set 101, an arterial chamber 102, a pump 103, a station 104 for adding a pharmaceutical product or additive such as heparin or the like, a venous chamber 105, a blood chamber 106a (and a sensor 106b attached thereto, such as a CLiC™ device for measuring pertinent information in the system 100), and so on, where these parts are known in the art and as such will not be described further herein. FIG. 1 also shows the arterial line 107 and the venous line 108 entering and exiting a dialyzer 110, as well as the dialysate lines 109 entering and exiting a dialyzer 110, with arrows showing the direction of the blood flow and dialysate flow within the example system 100.

The dialyzer 110 may thus include a plurality of ports for connections to tubing for the blood lines and the dialysate lines. And, as shown in FIG. 1, the dialyzer 110 may include at least four ports—e.g., an inlet port for receiving blood from the arterial line 107, an outlet port for supplying blood back into the venous line 108, and ports for supplying and draining dialysate to and from the dialyzer 110.

Two connection regions for coupling tubing to ports of the dialyzer 110 are shown in FIG. 1—a first connection region 111 at the inlet port, and a second connection region 112 at the outlet port. Aspects of the present teachings may be particularly advantageous for securing these connection regions, as they can represent some of the most critical junctions for a dialysis system 100. That is, these connection regions may be particularly prone to disconnecting, leaking, or otherwise failing, which can have dire consequences for a patient and/or a treatment session—e.g., air infiltrating these ports can lead to an embolism. Thus, aspects of the present teachings may be used to secure one or more of these connections to mitigate or prevent such failures. Aspects of the present teachings may also or instead be used to ensure that these ports are properly engaged with tubing and/or connectors coupled therewith. However, it will be understood that aspects of the present teachings may also or instead be used to secure other ports of the dialyzer 110 and/or other connections/junctions in the system 100 or similar systems.

Specific connectors may be used for securing tubing to a port in the system 100. For example, the first connection region 111 at the inlet port and the second connection region 112 at the outlet port typically utilize a specific type of connector—i.e., a connector complying with standards set by the German Institute for Standardisation (DIN)—for coupling the port of the dialyzer 110 with tubing in the system 100. These connectors may have a specific size and/or shape, as well as specific features, some of which are described below with reference to FIG. 2.

FIG. 2 illustrates a connector. The connector 200 may comply with standards set by the German Institute for Standardisation (DIN) for extracorporeal circuits of dialysis systems such as the system 100 shown in FIG. 1, where these connectors are typically referred to in the art as "DIN connectors." Turning back to FIG. 2, and as explained above, the connector 200 may have a specific size and shape, and may include specific features in order to meet the aforementioned DIN standards or otherwise.

In general, the connector 200 may include a first end 201 structurally configured to couple to tubing—e.g., tubing such as intravenous (IV) tubing made from any suitable material, including without limitation, one or more of polypropylene, nylon, dynaflex, and the like. For example, the first end 201 of the connector 200 may include a void 203 sized and shaped to receive a tube therein (e.g., via a friction fit or other securement means), and/or the first end 201 of the connector 200 may itself be sized and shaped to fit within an open end of tubing for engagement (e.g., via a friction fit or other securement means) such as by having a substantially cylindrical shape mimicking the shape of an end of tubing, where the tubing (through an elastic property thereof) can flex about the first end 201.

The connector 200 may include a second end 202 structurally configured to releasably secure the connector 200 to a port of a dialyzer, or other similar device. Specifically, the second end 202 of the connector 200 may include threading 204 (e.g., external threading for a male end as shown in the figure, or internal threading for a female end) that engages with corresponding threading, grooves, and/or other features (e.g., bearings) disposed (directly or indirectly) on a port of a dialyzer. The threading may comply with a standard for coupling, such as through including features for a Luer lock fitting or the like.

The connector 200 may include a pair of flanges 205 forming a winged portion 206 of the connector 200 disposed between the first end 201 and the second end 202 of the connector 200. This winged portion 206 may form the widest portion of the connector 200—i.e., where a diameter from an apex of one flange 205 to an apex of an opposing flange is greater than a diameter of one or both of the first end 201 and the second end 202 of the connector 200. The winged portion 206 may be structurally configured for a user (e.g., a care provider, a medical technician, and/or a patient) to grasp for holding and rotating the connector 200 to secure and/or remove the connector 200 to/from a component to which its configured to be releasably secured, such as a port of a dialyzer.

Thus, in the context of FIGS. 1 and 2, certain aspects of the present teachings may aid in providing and securing a connector 200 (and tubing coupled thereto) to a port of a dialyzer 110, such as at the first connection region 111 at the inlet port and the second connection region 112 at the outlet port. That is, an aspect of the present teachings may be used to secure a connection between a dialyzer 110 and a connector 200 (e.g., a DIN connector) that will result in a relatively safe hemodialysis treatment by alleviating or preventing the severing of such junctions.

Aspects of the present teachings may thus include a device for securing a connection to a dialyzer. By way of example, the device may have the ability to be inserted onto a cap of a dialyzer in which one or more ports of the dialyzer are situated. The device may thus include an engagement portion for coupling the device to the cap (or other portion) of the dialyzer. Further, because a port of the dialyzer may be configured for engagement with a DIN connector (such as that described above with reference to FIG. 2), the device may include a portion structurally configured to receive at least a portion of the DIN connector therein. And more particularly, the device may have the ability to be inserted onto a dialyzer cap, and the device may have the shape of a portion of a DIN connector on its inside for proper alignment therewith. The device may be configured for engagement with a dialyzer cap and DIN connector after the DIN connector is fully engaged with a dialyzer port.

The device may be configured for use with any hemodialysis treatment that includes a dialyzer and a connector such as a DIN connector. In general, the device (or other aspects of the present teachings) may be able to provide numerous advantages in the art including preventing leaks (e.g., blood leaks) during treatment, securing a connection, ensuring a preferred engagement in a connection, being user friendly and intuitive, and more.

Figure 3:
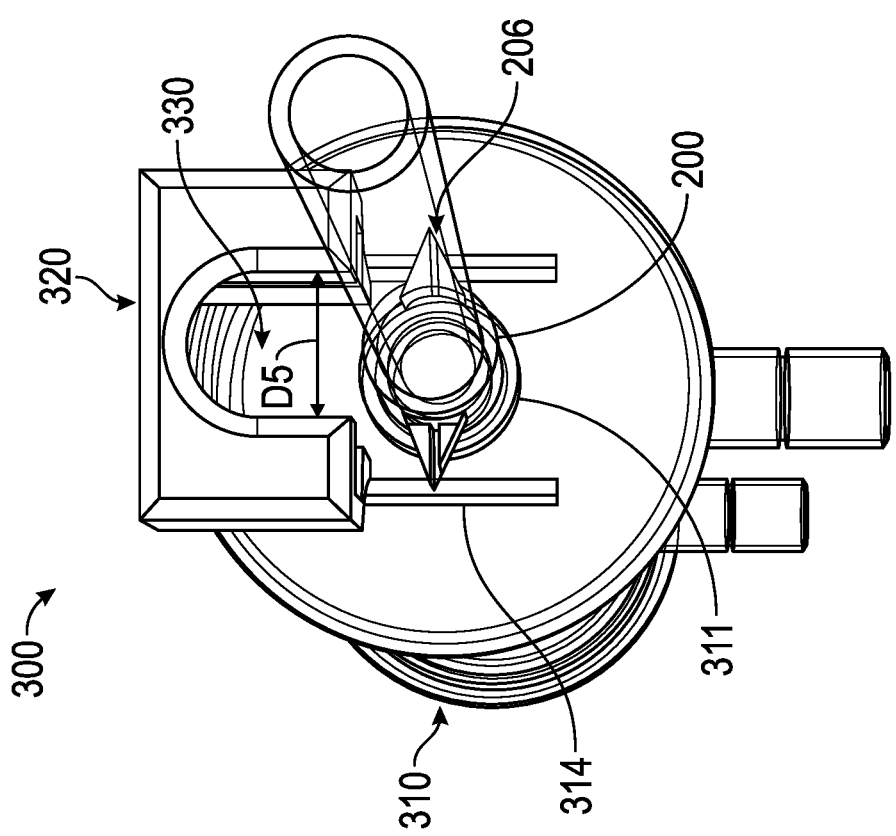
FIG. 3 illustrates a locking device being inserted onto a dialyzer, in accordance with a representative embodiment.
Figure 4:
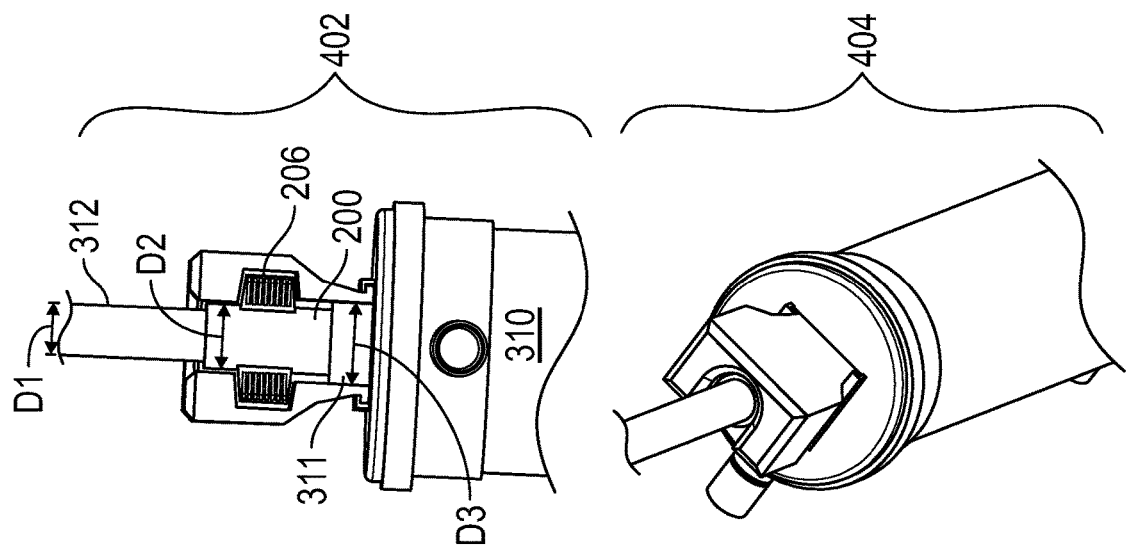
FIG. 4 illustrates various views of a locking device securing a connection of a dialyzer, in accordance with a representative embodiment.
Figure 4:
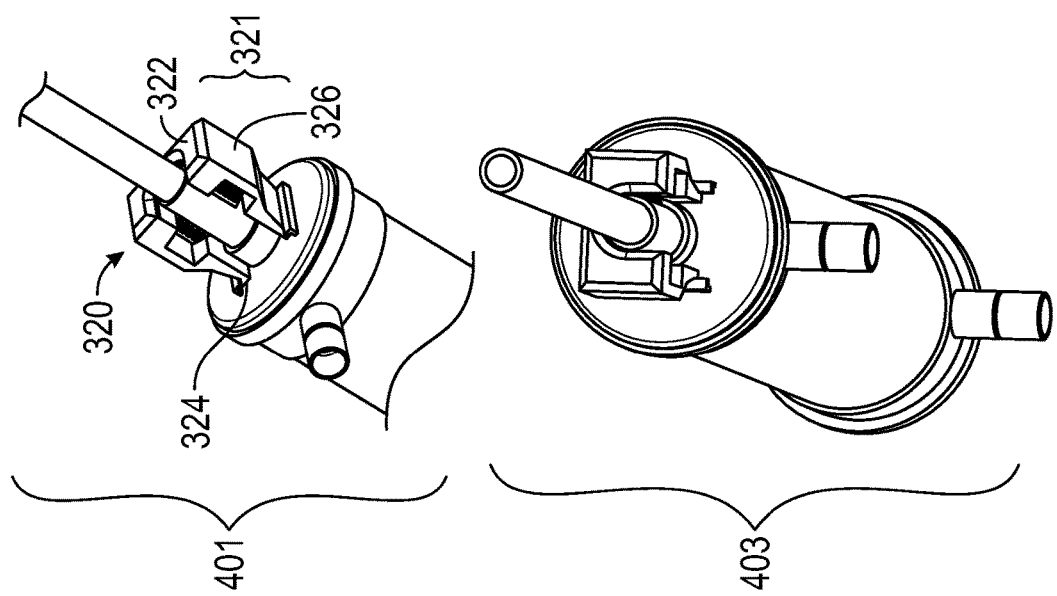
Figure 6:
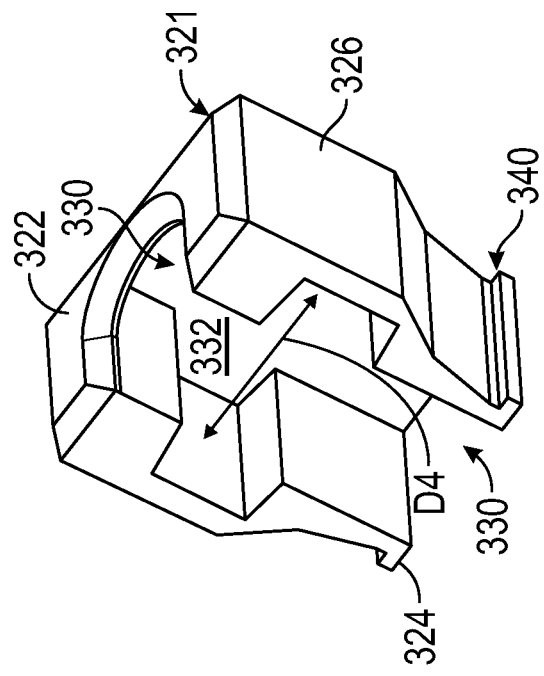
FIG. 6 illustrates a front perspective view of a device for securing a connection to a dialyzer, in accordance with a representative embodiment.
Figure 7:
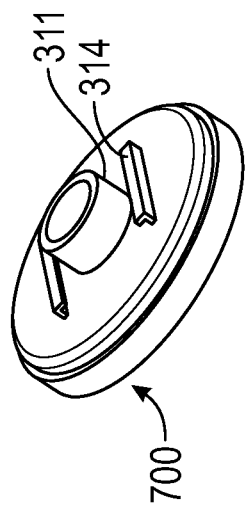
FIG. 7 illustrates a cap of a dialyzer, in accordance with a representative embodiment.
Figure 5:
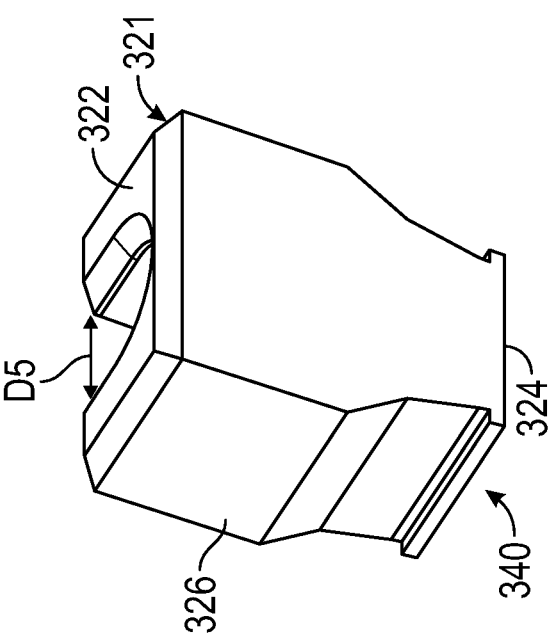
FIG. 5 illustrates a rear perspective view of a device for securing a connection to a dialyzer, in accordance with a representative embodiment.

FIG. 3 illustrates a locking device being inserted onto a dialyzer, in accordance with a representative embodiment; FIG. 4 illustrates various views of a locking device securing a connection of a dialyzer, in accordance with a representative embodiment; FIG. 5 illustrates a rear perspective view of a device for securing a connection to a dialyzer, in accordance with a representative embodiment; FIG. 6 illustrates a front perspective view of a device for securing a connection to a dialyzer, in accordance with a representative embodiment; and FIG. 7 illustrates a cap of a dialyzer, in accordance with a representative embodiment. Collectively, FIGS. 3-7 show a system 300 for securing a connection to a dialyzer 310, or portions thereof. In general, the system 300 may include a locking device 320 (which may otherwise be referred to herein simply as a "device") and at least a portion of the dialyzer 310 or a component coupled thereto.

The locking device 320 may, in general, be structurally configured to secure a connection to a dialyzer 310—e.g., a connection to a port 311 of the dialyzer 310. More specifically, and as shown in the figures, the port 311 may be an inlet port and/or an outlet port of the blood line of a dialysis system or the like. Also or instead, the port 311 may be one or more ports for supplying and draining dialysate to and from the dialyzer 310, or another port of the dialyzer 310. In general, once a connector 200—which may be a DIN connector as described herein and known in the art—is placed in a predetermined engagement with the port 311 of the dialyzer 310, the locking device 320 may maintain this predetermined engagement between the connector 200 and the port 311. That is, the locking device 320 may lock the position of the connector 200 relative to the dialyzer 310 thereby securing the connection from being inadvertently disengaged or otherwise compromised, e.g., during a hemodialysis treatment or the like. To this end, and as explained in more detail herein, the locking device 320 may include a shape corresponding to that of the connector 320 on its inside to allow these elements to collectively create a go-no-go fixture. This can ensure that the connector 320 does not become disconnected while the fixture is being used.

As best shown in FIG. 4 (where FIG. 4 includes a first view 401, a second view 402, a third view 403, and a fourth view 404 of the system 300) as well as can be seen in FIGS. 5-6, the locking device 320 may include a housing 321 having a top surface 322, a bottom surface 324, and a side portion 326 disposed between the top surface 322 and the bottom surface 324. The housing 321 may be structurally configured to be reusable for a plurality of dialysis treatments. In other words, the locking device 320 may be configured to be reusable—e.g., it may be washable and/or sterilizable. Also or instead, the housing 321 may be made of plastic—e.g., the locking device 320 may be a plastic molded component.

As best shown in FIG. 6, the locking device 320 may include a cutout 330 disposed through the housing 321 from the top surface 322 to the bottom surface 324. As best shown in FIG. 4, the cutout 330 at the bottom surface 324 of the locking device 320 may be sized and shaped to accommodate a port 311 of a dialyzer 310. And, the cutout 330 at the top surface 322 may be sized and shaped to accommodate one or more of (i) an outer diameter D1 of tubing 312 of an extracorporeal circuit of a dialysis system, (ii) an outer diameter D2 of a first end of a connector 200 configured to couple the tubing 312 to the port 311 of the dialyzer 310, and (ii) an outer diameter D3 of the port 311 of the dialyzer 310, where, as described above, the second end of the connector 200 may oppose the first end and may be configured to releasably secure the connector 200 to the port 311 of the dialyzer 310. Stated otherwise, the cutout 330 may be sized and shaped to receive at least a portion of one or more of the following therein: the port 311, the tubing 312, and the connector 200.

As best shown in FIG. 6, the locking device 320 may further include an interior void 332 within the side portion 326 between the top surface 322 and the bottom surface 324 of the housing 321. The interior void 332 may have a maximum diameter D4 that is larger than a maximum width D5 of the cutout 330 (see FIG. 5). That is, using the dimensions shown generally in FIGS. 3-6, D5 may be greater than one or more of D1, D2, and D3; and D4 may be greater than each of D1, D2, D3, and D5. In this manner—and as best shown in the first and second views 401, 402 of FIG. 4—the interior void 332 may be sized and shaped to accommodate winged portions 206 disposed between the first and second ends of the connector 200. In some implementations, a cross-section of at least a portion of the interior void 332 has substantially the same shape as a cross-section of the connector 200 disposed through the winged portions 206 thereof. Thus, in certain aspects, the locking device 320 may be mechanically keyed with at least a portion of the connector 200, e.g., through a size and shape of the interior void 332 that corresponds to a size and shape of the connector 200.

As best shown in FIGS. 5 and 6, the locking device 320 may further include a first engagement portion 340 disposed on or near (e.g., adjacent to) the bottom surface 324 of the housing 321. The first engagement portion 340 may be structurally configured to couple to a second engagement portion 314 disposed on an end of the dialyzer 310 that includes the port 311—e.g., the second engagement portion 314 may be disposed on a cap 700 for a dialyzer as shown in FIG. 7. And, in this manner, the engagement portions may be structurally configured such that, when these engagement portions are coupled, the connector 200 may be at least partially disposed within the interior void 332 and the winged portions 206 of the connector 200 may be mitigated from rotating relative to the end of the dialyzer 310 thereby securing the connector 200 in a substantially fixed rotational position, where this configuration is best shown in the first and second views 401, 402 of FIG. 4. Thus, when the connector 200, and more particularly the winged portions 206 thereof, is disposed within the locking device 320 with the locking device 320 secured to the dialyzer 310 (e.g., a cap 700 thereof), the position of the connector 200 (and more specifically, the rotational position of the connector 200 relative to the dialyzer 310) may be maintained. This may mitigate or outright prevent rotational movement of the connector 200 thereby securing the junction between the connector 200 and the port 311 of the dialyzer 310.

The first engagement portion 340 may include a void structurally configured to receive a projection of the second engagement portion 314. For example, the first engagement portion 340 may include a void in the form of a slot or the like that is structurally configured to slidably receive a rail or the like of the second engagement portion 314. Similarly, the first engagement portion 340 may include a projection structurally configured to be received within a void of the second engagement portion 314. And, for example, the first engagement portion 340 may include a rail structurally configured to be slidably received by a slot of the second engagement portion 314. One or more of the first engagement portion 340 and the second engagement portion 314 may instead include a combination of one or more voids and one or more projections.

In some aspects, the first engagement portion 340 wholly forms the bottom surface 324 of the housing 321. That is, the size and shape of the bottom surface 324 of the housing 321 may be used for the first engagement portion 340. In some aspects, the housing 321 may be manipulated to facilitate engagement of the first engagement portion 340 and the second engagement portion 314. For example, the housing 321 may be flexed to facilitate the engagement, which can be accomplished by a user squeezing the housing during the engagement and/or to initiate the engagement.

As stated above, the locking device 320 may be used to ensure that a proper engagement/coupling is present between the connector 200 and the port 311 of the dialyzer 310. To this end, one or more of the cutout 330, the interior void 332, and the first engagement portion 340 may be structurally configured to prevent at least one of (i) coupling with the second engagement portion 314, and/or (ii) receiving the winged portions 206 of the connector 200 within the interior void 332 unless the connector 200 is in a predetermined position relative to the port 311 of the dialyzer 310. The predetermined position may be a fully seated position of the connector 200 relative to the port 311 of the dialyzer 310—e.g., where the connector 200 is disposed at a predetermined depth within the port 311, and/or where the connector 200 has been subjected to a predetermined number of rotations relative to the port 311, and the like. In this manner, using the locking device 320 may provide an initial check that can ensure that one or more connections are proper within the system 300.

As discussed above, FIG. 7 shows a portion of a dialyzer that includes a second engagement portion 314 as described herein—and, more specifically, FIG. 7 shows a cap 700 of a dialyzer. As such, it will be understood that the second engagement portion 314 may located on an end of the dialyzer that includes the port 311, where the first engagement portion 340 and the second engagement portion 314 are couplable such that the winged portions (and/or one or more other distinguishing features) of the connector are mitigated from rotating relative to the end of the dialyzer thereby securing the connector in a substantially fixed rotational position. As shown in the example embodiment of FIG. 7, the second engagement portion 314 may be integral with a housing of the dialyzer—e.g., the second engagement portion 314 may be integral with the cap 700 of a dialyzer or the like. Also or instead, and as explained in more detail below, the second engagement portion 314 may be disposed on an adapter couplable to a dialyzer.

Figure 9:
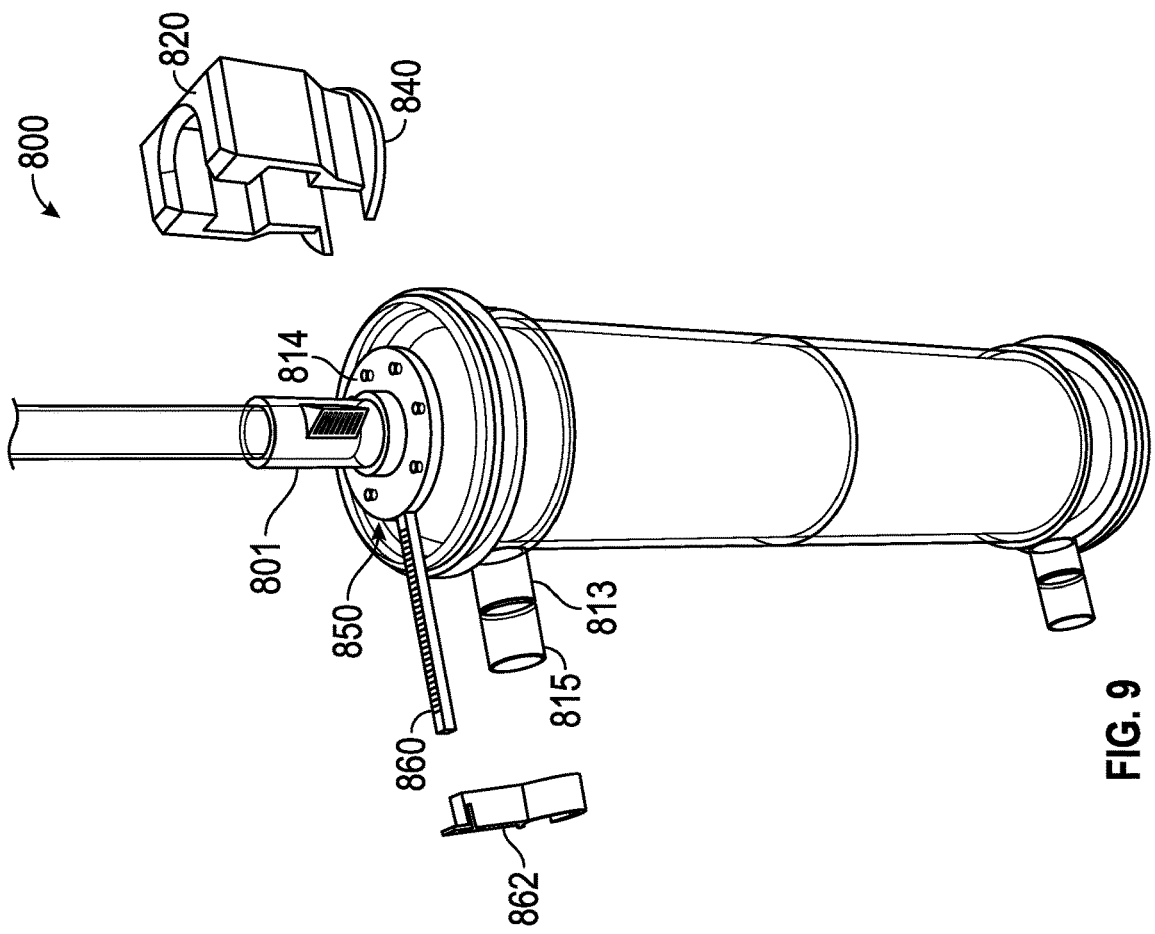
FIG. 9 illustrates a partially exploded view of a system for securing a connection of a dialyzer, in accordance with a representative embodiment.
Figure 8:
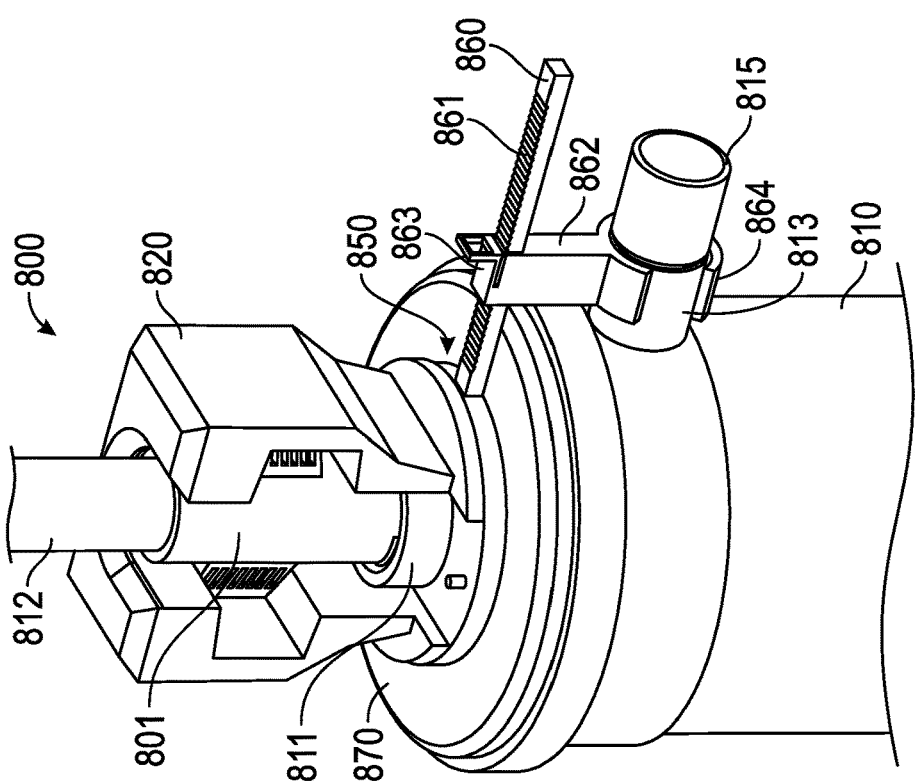
FIG. 8 illustrates a locking device securing a connection of a dialyzer, in accordance with a representative embodiment.
Figure 11:
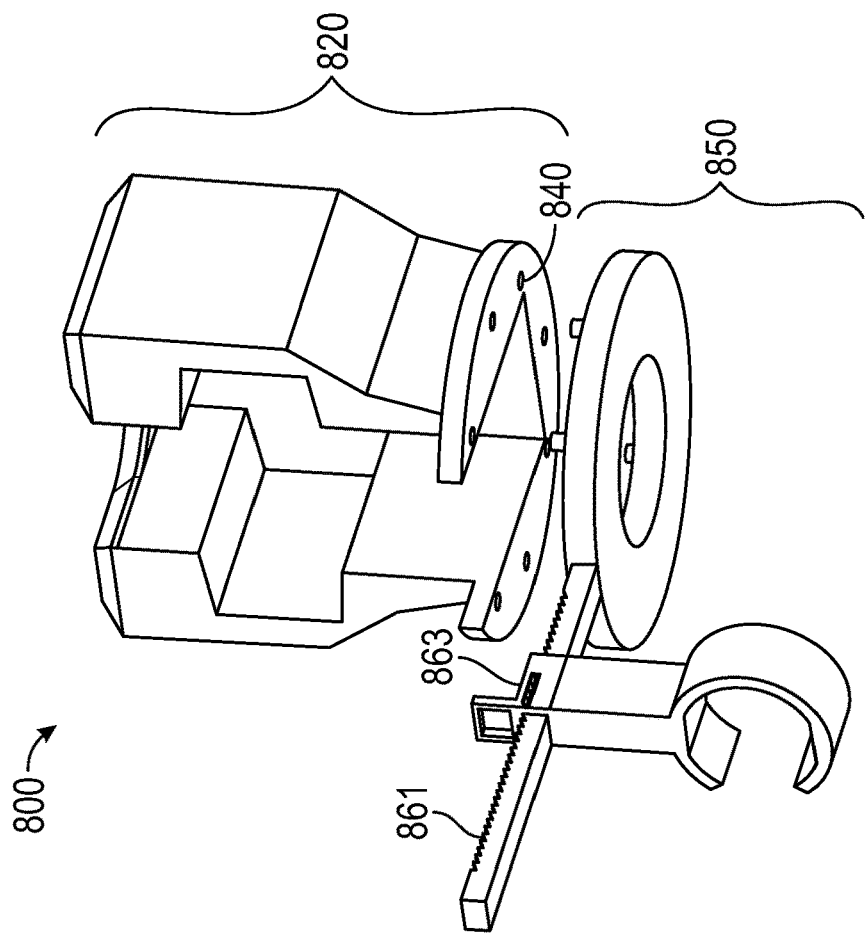
FIG. 11 illustrates another perspective view of a device and an adapter for securing a connection to a dialyzer, in accordance with a representative embodiment.
Figure 10:
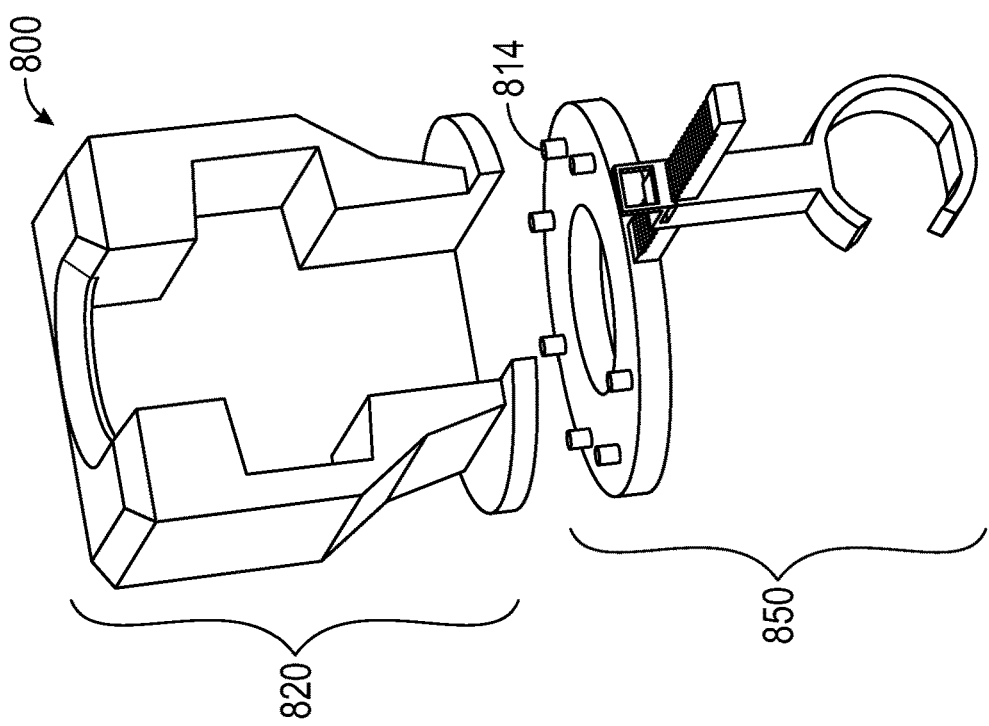
FIG. 10 illustrates a perspective view of a device and an adapter for securing a connection to a dialyzer, in accordance with a representative embodiment.

FIG. 8 illustrates a locking device securing a connection of a dialyzer, in accordance with a representative embodiment; FIG. 9 illustrates a partially exploded view of a system for securing a connection of a dialyzer, in accordance with a representative embodiment; and FIGS. 10 and 11 illustrates perspective views of a device and an adapter for securing a connection to a dialyzer, in accordance with a representative embodiment. The systems 800 generally shown in FIGS. 8-11 may feature a locking device 820, which may be the same or similar to that shown and described above with reference to FIGS. 3-7. And, as such, it will be understood that the systems 800 and/or locking devices 820 shown in FIGS. 8-11 may include any of the features shown and described above with reference to FIGS. 3-7, and vice-versa. The systems 800 may also include an adapter 850 as described herein. The adapter 850 may generally include the second engagement portion 814 as described herein, and the adapter 850 may be structurally configured to couple to a dialyzer 810 (e.g., a cap 870 thereof). In this manner, the adapter 850 may provide a portion of the system 800 that can be used to retrofit an existing dialyzer 810 for engaging with the locking device 820 to secure a connection to a port 811 of the dialyzer 810—e.g., the junction of a connector 801 (e.g., a DIN connector) with the port 811 for connecting tubing 812 to the port 811. As such, it will be understood that the locking device 820 may be provided in a kit or the like that also includes such an adapter 850, e.g., for retrofitting dialyzers 810 for use of a locking device 820.

The adapter 850 may be structurally configured to secure to an end (or other portion) of a dialyzer 810 that includes a port 811. For example, the adapter 850 may have an annular shape that is structurally configured to be disposed about (e.g., completely or partially encircle) the port 811 of the dialyzer 810. And, in such a configuration, the second engagement portion 814 may be disposed at least partially around the annular shape of the adapter 850. In an aspect, the annular shape of the adapter 850 may create a secure fit around the port 811 to create an engagement between the adapter 850 and the dialyzer 810, e.g., a secure friction fit. Other shapes for the adapter 850 are also or instead possible, as are other securement means as described herein.

As discussed above, the adapter 850 may include the second engagement portion 814 thereon, where the second engagement portion 814 is structurally configured to couple to the first engagement portion 840 of the locking device 820. And where, when so coupled, the connector 801 may be at least partially disposed within the interior void of the locking device 820 such that the winged portions of the connector 801 are mitigated from rotating relative to the end of the dialyzer 810 thereby securing the connector 801 in a substantially fixed rotational position. One or more of the first engagement portion 840 and the second engagement portion 814 may be any as described herein—e.g., including one or more of the following to facilitate engagement therebetween: a void, a projection, a clamp, a clip, a dowel, a component structurally configured to create a friction fit or the like, an adhesive, a hook and loop fastener, a latch, a pin, a screw, a slider, a component structurally configured to create a snap fit or the like, one or more magnets, and so forth.

The system 800 may further include an extension 860 engaged with the adapter 850. The extension 860 may generally include a cantilevered arm or the like upon which another engagement feature can move, e.g., for adjusting and/or accommodating a coupling between the adapter 850 and the dialyzer 810. To this end, in some aspects, the extension 860 may include a mating feature 862 structurally configured to couple with a portion of a dialysis system. For example, the mating feature 862 may include one or more of a clamp and a clip 864 structurally configured to couple to a portion of the dialyzer 810. By way of further example, the mating feature 862 may include a clip 864 or the like that is structurally configured to couple with at least one of a dialysate port 813 (or another port) and dialysate tubing 815 (or other tubing, cabling, or otherwise) of a dialysis system. The mating feature 862 may also or instead engage with another portion or fixture of the dialyzer 810 or a component coupled thereto.

The mating feature 862 may be movable (e.g., slidable) along the extension 860 for adjusting the position of the mating feature 862. For example, the extension 860 may include a plurality of teeth 861 or the like that engage with a pawl 863 or the like connected to the mating feature 862, e.g., similar to how a cable tie functions. That is, the mating feature 862 and the extension 860 may collectively form a ratchet so that a position of the mating feature 862 relative to the extension 860 can be permanently or temporarily maintained. For example, for a temporary positioning mechanism, the mating feature 862 may include a tab or the like that can be depressed or otherwise activated to release the ratchet so that the mating feature 862 can be moved along the extension 860. The mating feature 862 may otherwise be adjustable relative to the extension 860, or the locking device 820 generally, for accommodating an engagement between the adapter 850 and the dialyzer 810.

Other techniques for securing the adapter 850 to the dialyzer 810 may also or instead be used. For example, the adapter 850 may include an adhesive or the like thereon for securing the adapter 850 to the end of the dialyzer 810. In general, the adapter 850 may be engageable with the dialyzer 810 in a substantially fixed relationship such that engaging the locking device 820 with the adapter 850 maintains a substantially fixed relative position of the locking device 820 and the dialyzer 810. Numerous engagement techniques may be utilized for this purpose as will be understood by a skilled artisan, including any of those mentioned herein, e.g., with reference to the first and second engagement features.

FIGS. 12-16 generally illustrate a sequence of operation for securing a connection of a dialyzer, in accordance with a representative embodiment. As discussed above, embodiments of the present teachings including a kit or the like having a locking device 1220 and an adapter 1250 may be used with different blood lines and dialyzers across different markets, without a need to modify a dialyzer 1210 (e.g., an end cap 1215 of the dialyzer 1210 may be unmodified). That is, an existing dialyzer 1210, which may be unmodified from its manufactured state, may be retrofitted via the adapter 1250 such that the locking device 1220 can secure a junction between tubing 1212 (e.g., tubing 1212 used to form at least part of an extracorporeal circuit of a dialysis system) and a port 1211 of the dialyzer 1210—and more specifically, a junction between a connector 1201 and a port 1211 of the dialyzer 1210 may be secured as described herein. The example sequence of operation shown in FIGS. 12-16 demonstrates such retrofitting and securement of the junction between the connector 1201 and the port 1211 of the dialyzer 1210.

Figure 13:
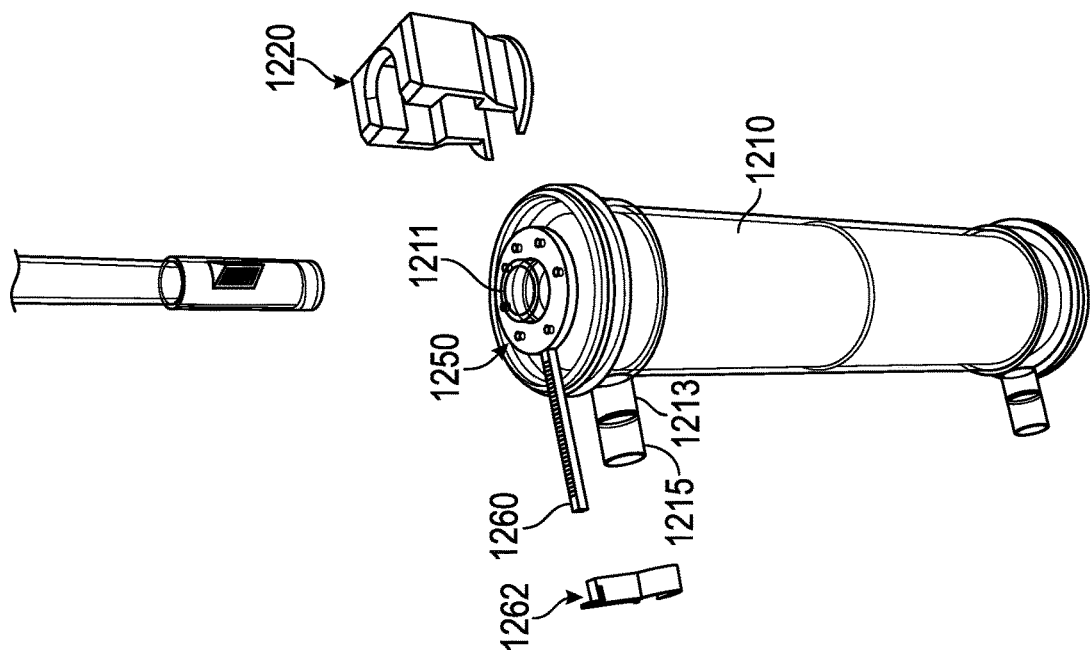
FIG. 13 illustrates a portion of a sequence of operation for securing a connection of a dialyzer, in accordance with a representative embodiment.
Figure 12:
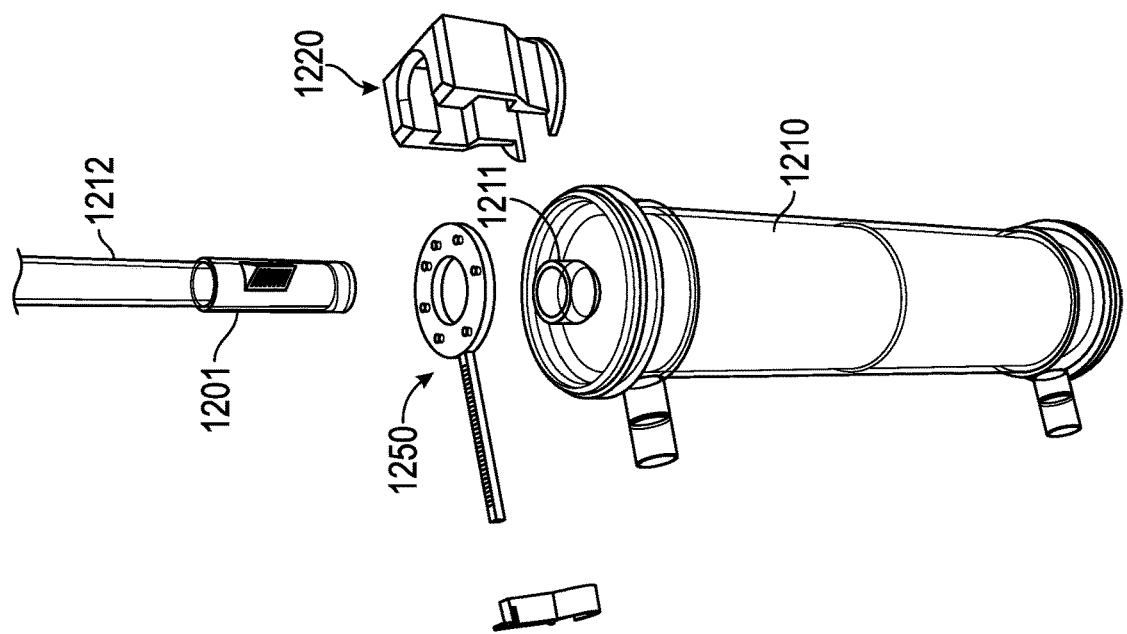
FIG. 12 illustrates a portion of a sequence of operation for securing a connection of a dialyzer, in accordance with a representative embodiment.

As shown in FIG. 12, the items in the system or kit may be gathered for assembly, including the locking device 1220 and the adapter 1250. As shown in FIG. 13, the adapter 1250 may be placed for engagement with the dialyzer 1210. More specifically, in an aspect, the adapter 1250 is placed onto the portion of the dialyzer 1210 containing the port 1211 having a junction to be secured by the locking device 1220. An extension 1260 may be aligned over another portion of the dialyzer 1210, such as a dialysate port 1213 (or another port) and/or dialysate tubing 1215 (or other tubing/cabling), upon which a mating feature 1262 (such as a clip or the like) will engage. Other structures of the dialyzer 1210 or dialysis system may also or instead be used for affixing the adapter 1250 (e.g., via the extension 1260 or otherwise) to the dialyzer 1210.

Figure 15:
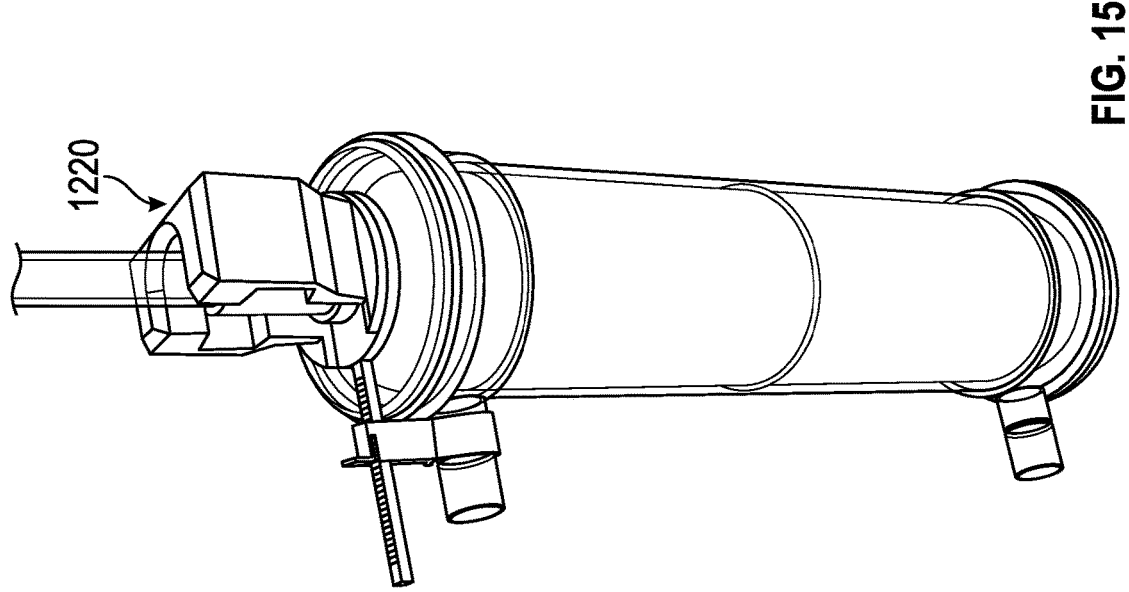
FIG. 15 illustrates a portion of a sequence of operation for securing a connection of a dialyzer, in accordance with a representative embodiment.
Figure 14:
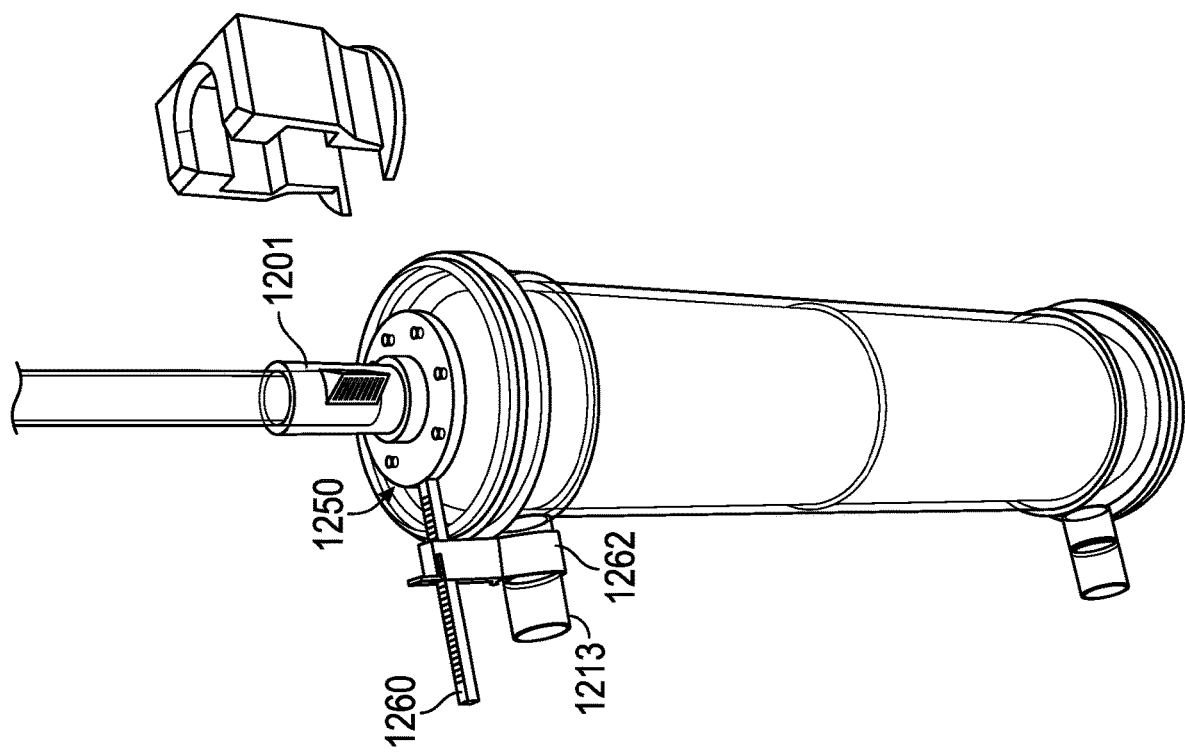
FIG. 14 illustrates a portion of a sequence of operation for securing a connection of a dialyzer, in accordance with a representative embodiment.
Figure 16:
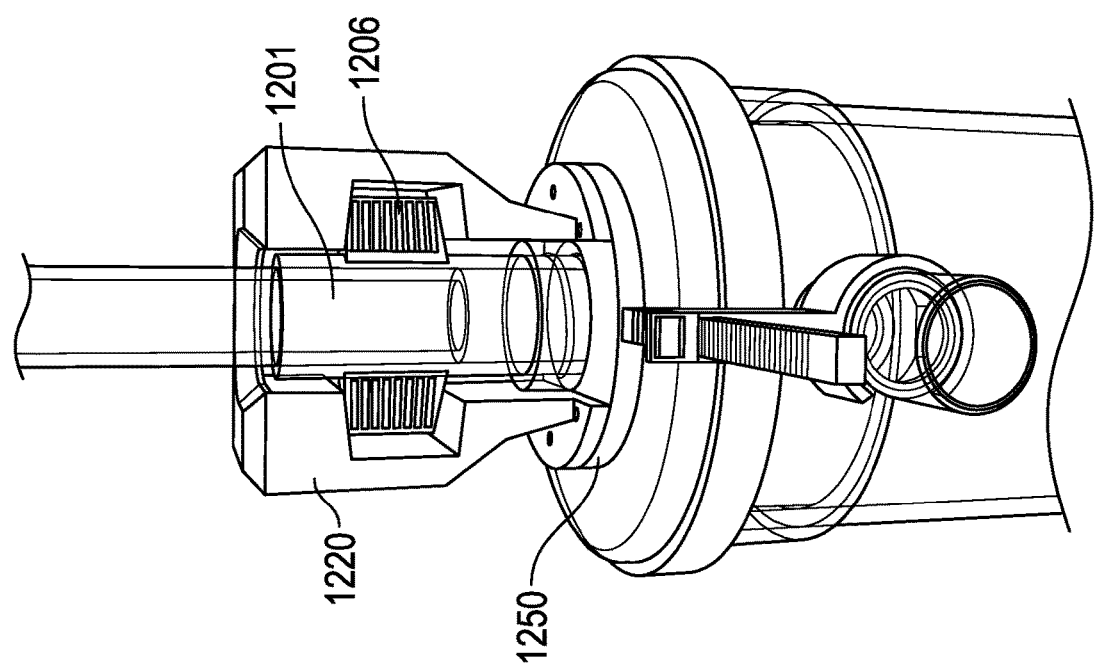
FIG. 16 illustrates a front view of a system for securing a connection of a dialyzer, in accordance with a representative embodiment.

As shown in FIG. 14, the adapter 1250 may be coupled to a fixture of the dialyzer 1210 or dialysis system such as through an engagement of the mating feature 1262 to the dialysate port 1213 or the like. That is, the mating feature 1262 may be placed upon, and moved along, the extension 1260 (via a ratcheting or the like as described herein) and coupled to the dialysate port 1213 such that it substantially maintains the position of the adapter 1250 relative to the port 1211 upon which the connector 1201 is inserted or otherwise coupled. As shown in FIG. 15, the locking device 1220 may then be aligned with and secured onto the adapter 1250 (e.g., via a mechanical coupling of engagement portions disposed on each of these elements) such that the locking device 1220 at least partially envelops the connector 1201, and where the position of the locking device 1220 is maintained relative to the dialyzer 1210 via the adapter 1250. FIG. 16 shows a view of the assembled locking device 1220 and adapter 1250, where the locking device 1220 includes at least a portion of the connector 1201 therein, including a winged portion 1206 thereof.

Figure 17:
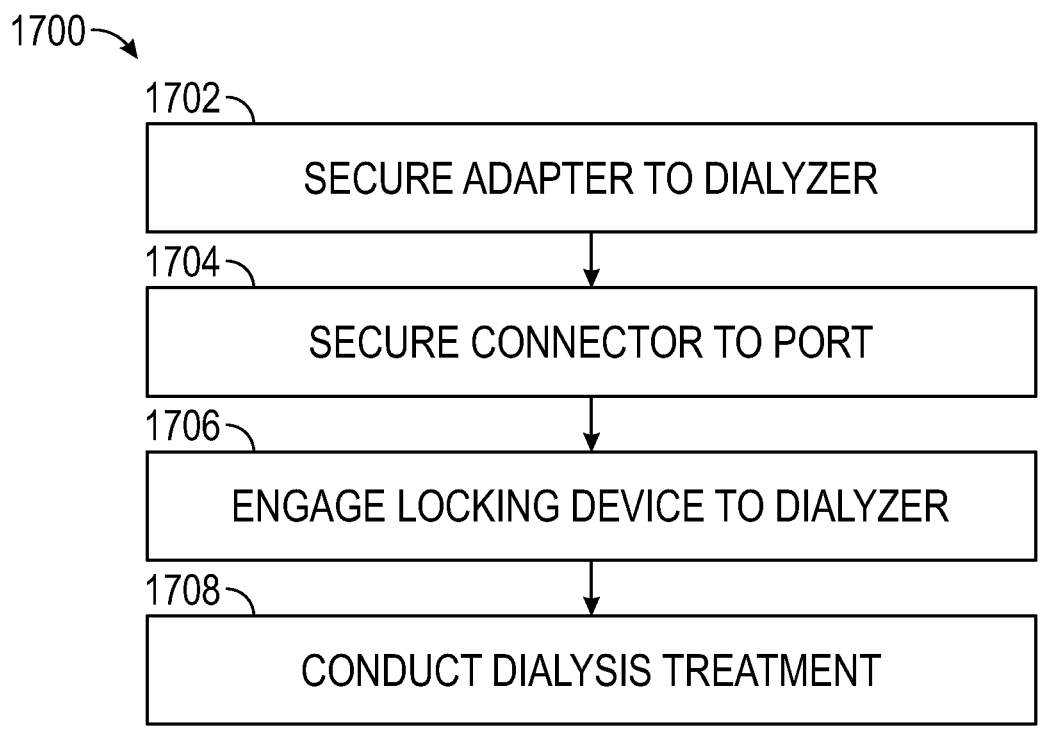
FIG. 17 is a flow chart of a method for securing a connection to a dialyzer, in accordance with a representative embodiment.

FIG. 17 is a flow chart of a method for securing a connection to a dialyzer, in accordance with a representative embodiment. The method 1700 may be performed using any one or more of the devices, systems, and kits as described herein. Thus, the method 1700 may be used to secure a connection to a port of a dialyzer of a dialysis treatment system—e.g., securing the junction between a connector and an inlet and/or outlet port of a blood line of the dialysis system.

As shown in step 1702, the method 1700 may include securing an adapter to a dialyzer, e.g., securing an adapter to an end of the dialyzer that includes a port that will have a junction that is desirous for securing, e.g., for safety or otherwise. As discussed herein, the adapter may include an engagement portion, e.g., a second engagement portion structurally configured for coupling with a first engagement portion on another device such as a locking device or the like. As discussed herein, securing the adapter may include coupling a mating feature thereof with a portion of a dialysis system. The mating feature may include one or more of a clamp and a clip; in this manner, securing the adapter may include coupling the mating feature with at least one of a dialysate port and dialysate tubing of the dialysis system. To this end, and as discussed herein, it will be understood that the method 1700 may further include adjusting the mating feature for coupling with a portion of the dialysis system.

As shown in step 1704, the method 1700 may include releasably securing a connector to a port of a dialyzer such that the connector is in a predetermined position relative to the port—e.g., a fully seated position. As described herein, the connector may have one or more winged portions disposed between first and second ends thereof. Releasably securing the connector to the port may include rotating the connector—e.g., via a winged portion thereof—relative to the port until the connector is in the predetermined position.

As shown in step 1706, the method 1700 may include engaging a locking device with the dialyzer, e.g., engaging the locking device to at least one of the port and the connector. This may also or instead include engaging the locking device with an adapter positioned on the dialyzer as described herein. The engagement of the locking device with the dialyzer may thus include coupling a first engagement portion disposed on the locking device to a second engagement portion disposed on an end of the dialyzer that includes the port (e.g., where the second engagement portion is disposed on an adapter disposed on the dialyzer). The engagement of the locking device with the dialyzer may further include receiving at least a portion of a winged portion of the connector within an interior void of a housing of the locking device as described herein. For example, engaging the locking device may include sliding the locking device onto the end of the dialyzer that includes the port, where this sliding mates engagement features disposed on each of the locking device and the dialyzer (directly or indirectly), and where this sliding also at least partially envelops the connector with the locking device. Also or instead, engaging the locking device may include mechanically keying the locking device onto the end of the dialyzer that includes the port, and/or mechanically keying the locking device with the connector.

As shown in step 1708, the method 1700 may include conducting a dialysis treatment using the dialyzer with a connection to a port thereof being secured by the locking device.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings.

Unless the context clearly requires otherwise, throughout the description, the words "comprise," "comprising," "include," "including," and the like are to be construed in an inclusive sense as opposed to an exclusive or exhaustive sense; that is to say, in a sense of "including, but not limited to." Additionally, the words "herein," "hereunder," "above," "below," and words of similar import refer to this application as a whole and not to any particular portions of this application.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y, and Z may include any method of directing or controlling any combination of such other individuals or resources to perform steps X, Y, and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It will be appreciated that the methods and systems described above are set forth by way of example and not of limitation. Absent an explicit indication to the contrary, the disclosed steps may be modified, supplemented, omitted, and/or re-ordered without departing from the scope of this disclosure. And, numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A system, comprising:
    a locking device, comprising:
        a housing including a top surface, a bottom surface, and a side portion disposed between the top surface and the bottom surface;
        a cutout disposed through the housing from the top surface to the bottom surface, the cutout at the bottom surface sized and shaped to accommodate a port of a dialyzer, and the cutout at the top surface sized and shaped to accommodate one or more of (i) an outer diameter of tubing of an extracorporeal circuit of a dialysis system, and (ii) an outer diameter of a first end of a connector configured to couple the tubing to the port of the dialyzer, wherein a second end of the connector is configured to releasably secure the connector to the port of the dialyzer;
        an interior void within the side portion between the top surface and the bottom surface of the housing, the interior void having a maximum diameter larger than a maximum width of the cutout, the interior void sized and shaped to accommodate winged portions disposed between the first and second ends of the connector; and
        a first engagement portion disposed on the bottom surface of the housing; and
    a second engagement portion on an end of the dialyzer that includes the port, the second engagement portion disposed on an adapter couplable to the dialyzer, wherein the first engagement portion and the second engagement portion are couplable such that the winged portions of the connector are mitigated from rotating relative to the end of the dialyzer thereby securing the connector in a substantially fixed rotational position.

2. The system of claim 1, wherein the second engagement portion is integral with a housing of the dialyzer.

3. The system of claim 1, wherein the adapter has an annular shape structurally configured to be disposed about the port of the dialyzer.

4. The system of claim 1, wherein the adapter comprises an extension including a mating feature structurally configured to couple with a portion of the dialyzer.

5. A device for securing a connection to a dialyzer, the device comprising:
a housing including a top surface, a bottom surface, and a side portion disposed between the top surface and the bottom surface;
a cutout disposed through the housing from the top surface to the bottom surface, the cutout at the bottom surface sized and shaped to accommodate a port of a dialyzer, and the cutout at the top surface sized and shaped to accommodate one or more of (i) an outer diameter of tubing of an extracorporeal circuit of a dialysis system, and (ii) an outer diameter of a first end of a connector configured to couple the tubing to the port of the dialyzer, wherein a second end of the connector is configured to releasably secure the connector to the port of the dialyzer;
an interior void within the side portion between the top surface and the bottom surface of the housing, the interior void having a maximum diameter larger than a maximum width of the cutout, the interior void sized and shaped to accommodate winged portions disposed between the first and second ends of the connector;
a first engagement portion disposed on the bottom surface of the housing, the first engagement portion structurally configured to couple to a second engagement portion disposed on an end of the dialyzer that includes the port such that, when coupled, the connector is at least partially disposed within the interior void and the winged portions of the connector are mitigated from rotating relative to the end of the dialyzer thereby securing the connector in a substantially fixed rotational position, and
an adapter structurally configured to secure to the end of the dialyzer that includes the port, the adapter including the second engagement portion thereon.

6. The device of claim 5, further comprising an extension engaged with the adapter, the extension including a mating feature structurally configured to couple with a portion of a dialysis system.

7. The device of claim 6, wherein the mating feature is adjustable along the extension, and wherein the mating feature includes one or more of a clamp and a clip structurally configured to couple with at least one of a dialysate port and dialysate tubing of the dialysis system.

8. The device of claim 5, wherein the adapter has an annular shape structurally configured to be disposed about the port of the dialyzer.

9. The device of claim 8, wherein the second engagement portion is disposed at least partially around the annular shape of the adapter.

10. The device of claim 5, wherein the first engagement portion includes at least one of: a void structurally configured to receive a projection of the second engagement portion, and a projection structurally configured to be received within a void of the second engagement portion.

11. The device of claim 5, wherein the first engagement portion includes at least one of: a slot structurally configured to slidably receive a rail of the second engagement portion, and a rail structurally configured to be slidably received by a slot of the second engagement portion.

12. The device of claim 5, wherein one or more of the cutout, the interior void, and the first engagement portion is structurally configured to prevent at least one of coupling with the second engagement portion and receiving the winged portions of the connector within the interior void unless the connector is in a predetermined position relative to the port of the dialyzer.

13. The device of claim 12, wherein the predetermined position is a fully seated position of the connector within the port of the dialyzer.

14. The device of claim 5, wherein the connector complies with standards set by the German Institute for Standardisation (DIN) for extracorporeal circuits of dialysis systems.

15. The device of claim 5, wherein the port of the dialyzer is an inlet port or an outlet port.

16. The device of claim 5, wherein a cross-section of at least a portion of the interior void has substantially the same shape as a cross-section of the connector disposed through the winged portions thereof.

17. The device of claim 5, wherein the first engagement portion wholly forms the bottom surface of the housing.

18. A method, comprising:
releasably securing a connector to a port of a dialyzer such that the connector is in a predetermined position relative to the port, the connector having one or more winged portions disposed between first and second ends thereof;
securing an adapter to an end of the dialyzer that includes the port, the adapter comprising a second engagement portion; and
engaging a locking device with at least one of the port and the connector by:
coupling a first engagement portion disposed on the locking device to the second engagement portion disposed on the end of the dialyzer; and
receiving at least a portion of the one or more winged portions of the connector within an interior void of a housing of the locking device.

19. The method of claim 18, wherein securing the adapter includes coupling a mating feature thereof with a portion of a dialysis system.

20. The method of claim 19, wherein the mating feature includes one or more of a clamp and a clip, and wherein securing the adapter includes coupling the mating feature with at least one of a dialysate port and dialysate tubing of the dialysis system.

* * * * *